(12) United States Patent
Tanaka et al.

(10) Patent No.: US 6,663,949 B1
(45) Date of Patent: Dec. 16, 2003

(54) DEODORIZING ABSORBENT SHEET

(75) Inventors: Masahito Tanaka, Tochigi (JP);
Mayumi Kimura, Tochigi (JP);
Futoshi Teranishi, Tochigi (JP);
Mitsugu Hamajima, Tochigi (JP);
Minoru Nakanishi, Tochigi (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/673,370
(22) PCT Filed: Jul. 9, 1999
(86) PCT No.: PCT/JP99/03721
§ 371 (c)(1),
(2), (4) Date: Oct. 16, 2000
(87) PCT Pub. No.: WO00/04938
PCT Pub. Date: Feb. 3, 2000

(30) Foreign Application Priority Data

Jul. 24, 1998 (JP) ............................................... 10-209795

(51) Int. Cl.⁷ ............................ B32B 5/16; B32B 23/04; B32B 21/04; B05D 1/12; B05D 1/36
(52) U.S. Cl. ..................... 428/323; 428/327; 428/340; 428/341; 428/342; 428/532; 428/537.1; 428/905; 442/96; 427/180; 427/201
(58) Field of Search ................................. 428/105–107, 428/114, 323, 327, 331, 340–342, 411.1, 500, 688, 689, 905, 532, 537.1; 427/541, 544, 180, 201, 203, 372.2; 442/60, 86, 96, 118, 121, 123, 153

(56) References Cited

U.S. PATENT DOCUMENTS 3,567,118 A   3/1971   Shepherd et al. .............. 239/6
4,198,648 A   4/1980   Nishizawa ..................... 357/43
5,230,958 A   7/1993   Dabi ........................... 428/402
5,972,808 A * 10/1999   Groeger et al. ................ 442/72

FOREIGN PATENT DOCUMENTS

| EP | 0 278 410 A1 | 8/1988 | ........... H01L/27/08 |
| EP | 0528248 | 2/1993 | |
| EP | 0661030 | 7/1995 | |
| EP | 0719531 | 7/1996 | |
| GB | 2093352 | 9/1982 | |
| JP | 63093350 | 4/1988 | |
| JP | 08281042 | 10/1996 | |
| WO | WO9746195 | 12/1997 | |

OTHER PUBLICATIONS

Patent Abstracts of Japan: vol. 013, No. 541 (E–854), Dec. 5, 1989 & JP 01 222484 A (SONY CORP), Sep. 5, 1989 abstract; figures.

Patent Abstracts of Japan vol. 018, No. 673 (E–1647), Dec. 19, 1994 & JP 06 268236 A (TOKIN CORP), Sep. 22, 1994 abstract; figure 11.

Patent Abstract of Japan vol. 013 No. 404 (E–817) Sep. 7, 1989 & JP 01 145846 A (Semiconductor Res Found; Others: 01), Jun. 7, 1989 Abstract figures.

* cited by examiner

Primary Examiner—Paul Thibodeau
Assistant Examiner—Sheeba Ahmed
(74) Attorney, Agent, or Firm—Birch, Stewart, Kolasch & Birch, LLP

(57) ABSTRACT

A deodorizing absorbent sheet having a water-insoluble deodorizer and an absorbent polymer which are embedded in a fiber web, wherein the absorbent polymer is fixed to the fibers making up the fiber web. The deodorizer is fixed inside the fiber web via the absorbent polymer. The deodorizer and absorbent polymer are substantially absent on the surface of the absorbent sheet.

14 Claims, 2 Drawing Sheets

DEODORIZING ABSORBENT SHEET

This application is the national phase under 35 U.S.C. §371 of PCT International Application No. PCT/JP99/03721 which has an International filing date of Jul. 9, 1999, which designated the United States of America.

TECHNICAL FIELD

The present invention relates to a deodorizing absorbent sheet suited to use as an absorbent member of an absorbent article, an underlay of a pet's toilet, and the like.

BACKGROUND ART

Known deodorizing absorbent sheets of this type include the absorbent member of a sanitary napkin that comprises an absorbent polymer sandwiched by two pieces of absorbent paper containing activated carbon as disclosed in Japanese Patent Laid-open No. 142256/82; and a deodorizing sheet obtained by scattering activated carbon between sheets of paper coated with a hot-melt adhesive and uniting them into one body as disclosed in Japanese Patent Laid-open No. 281042/96.

In the absorbent member having the above-mentioned structure, a layer containing the absorbent polymer where liquid is to be absorbed and held is separate from a layer containing the activated carbon serving for deodorization. Therefore, it is only indirectly that the deodorizing effect is exerted on the liquid absorbed and held so that the efficiency of deodorization is unsatisfactory. In order to obtain a sufficient deodorizing effect, a large quantity of a deodorizer, such as activated carbon, would be required, which might fall off during use of the napkin.

Further, the layer containing the absorbent polymer of the absorbent member disclosed in the above publication has a structure in which the absorbent polymer particles are merely sandwiched between two sheets of absorbent paper. Therefore, an increased amount of the absorbent polymer for increasing the absorption efficiency would also fall off during use of the napkin.

DISCLOSURE OF INVENTION

Accordingly, an object of the present invention is to provide a deodorizing absorbent sheet having a high deodorizing function and a high absorbing function.

Another object of the present invention is to provide a deodorizing absorbent sheet which can contain increased amounts of a deodorizer and an absorbent polymer without involving a fear of their falling off.

The inventors of the invention have found that the above objects can be accomplished by embedding a deodorizer and an absorbent polymer in a mixed state in the inside of a fiber web and fixing the deodorizer by making use of the tack of the absorbent polymer.

The present invention provides a deodorizing absorbent sheet having a water-insoluble deodorizer and an absorbent polymer which are embedded in a fiber web, in which the absorbent polymer is fixed to the fibers making up the fiber web, and the deodorizer is fixed inside the fiber web via the absorbent polymer, the deodorizer and the absorbent polymer being substantially absent on the surface of the sheet.

The present invention also provide a preferred process for producing the above-described deodorizing absorbent sheet comprising the steps of scattering the absorbent polymer and the deodorizer on a wet lower fiber sheet either simultaneously or successively in any order, overlaying an upper fiber sheet thereon, and uniting the upper and lower fiber sheets into a unitary body by drying.

BEST MODE FOR CARRYING OUT THE INVENTION

Figure 1:
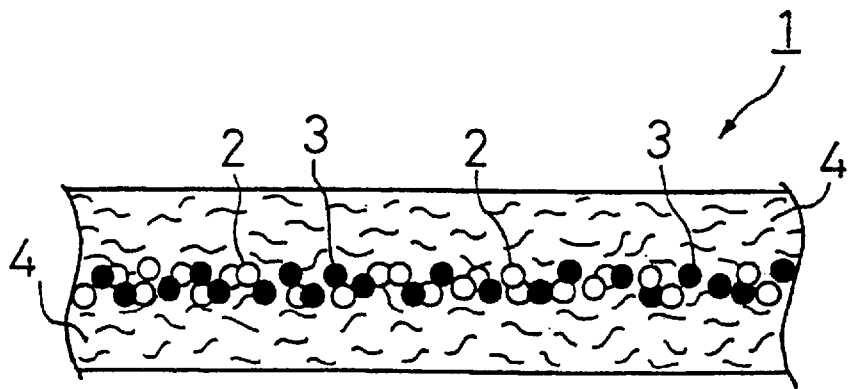
FIG. 1 is a schematic view showing the structure of the deodorizing absorbent sheet according to an embodiment of the present invention.

Preferred embodiments of the deodorizing absorbent sheet according to the present invention will be described by referring to the accompanying drawings. FIG. 1 is a schematic view showing the structure of the deodorizing absorbent sheet according to an embodiment of the present invention.

The deodorizing absorbent sheet 1 shown in FIG. 1 has a structure in which a water-insoluble deodorizer 2 and an absorbent polymer 3 make a layer embedded in a fiber web 4. That is, the deodorizing absorbent sheet 1 has a single sheet structure, which is entirely different from the structure stated above as to background art which is used in the sanitary napkin described in Japanese Patent Laid-open No. 142256/85, i.e., a 2-ply absorbent paper structure having absorbent polymer particles sandwiched in between two sheets of absorbent paper.

In the deodorizing absorbent sheet 1, the deodorizer 2 is adhered and fixed to the fibers constituting the fiber web 4 via the polymer 3. Neither the deodorizer 2 nor the polymer 3 is substantially present on the surface of the fiber web 4. The language "substantially absent (or substantially not present)" as used herein means that the deodorizer 2 and the polymer 3 do not substantially exist while it is acceptable for a trace amount of the deodorizer 2 and of the polymer 3 to be inevitably incorporated in the preparation of the deodorizing absorbent sheet 1.

Without being bound to any particular theory on the adhesion and fixation of the deodorizer 2 to the fiber via the polymer 3, it is considered that such adhesion and fixation is due to the complementary effect of the following phenomena (1) to (4).

(1) The polymer 3 deforms upon absorbing water and swelling. In more detail, the polymer 3 swells upon absorbing water and gets soft so as to change its shape to conform to the shape of the fiber or the deodorizer 2 which is present near the polymer 3, and then the polymer 3 adheres and fixes to the fiber or the deodorizer 2. In cases, a plurality of the polymer 3, while adhering to each other, enclose the fiber or the deodorizer 2. However, the entire surface of the deodorizer 2 is not coated with the polymer 3, because the polymer 3 has a large gel strength, and thus the deodorizer 2 is prevented from impairing the deodorizing property. In the case that drying of the polymer 3 proceeds while enclosing the fiber or the deodorizer 2, the state of the polymer 3 with enclosing them is maintained after drying up, so that the polymer 3 is firmly bonded to the fiber or the deodorizer 2. Even in the case that drying of the polymer 3 proceeds in such a state as merely adhering and fixing to the fiber or the deodorizer 2, the embedding of the polymer 3 due to the adhesion and fixation (i.e. anchor effect) and the intermolecular force allow the polymer 3 to bond to the fiber or the deodorizer 2 with sufficient strength.

(2) The polymer 3 swells and gets tacky, which contributes to the exhibition of the phenomenon (1) above.

(3) Polar groups in the polymer 3, particularly carboxyl groups, form hydrogen bonds. Accordingly, where the fiber and the deodorizer 2 has polar groups, the polymer 3 which swells and adheres to the fiber or the deodorizer 2 forms hydrogen bonds between the polymer 3 and the fiber or the deodorizer 2, resulting in the firm bonding of the polymer 3 to the fiber or the deodorizer 2.

(4) The polymer 3 in a form of fine particles is distributed over the entire area of the inside of the sheet 1. Accordingly, the phenomena (1), (2) and (3) above occur in every part of the sheet 1 to thereby effectively prevent the deodorizer 2 from falling off.

Both the deodorizer 2 and the polymer 3 are dispersed in a space formed by the fibers making up the fiber web 4 and exist with a prescribed thickness in the thickness direction of the fiber web 4. In other words, both the deodorizer 2 and the polymer 3 are dispersed in the inside of the fiber web 4 to form a three-dimensional layer. It follows that they can fully perform their absorbing and deodorizing functions and, moreover, the polymer 3 is effectively prevented from causing gel blocking.

As shown in FIG. 1, the deodorizer 2 and the polymer 3 are present in a mutually mixed state in the inside of the fiber web 4. Accordingly, the deodorizing absorbent sheet 1 performs the function of absorbing and holding liquid and the function of deodorizing the liquid in the same site to exhibit extremely increased deodorizing efficiency. That is, absorbing and holding liquid and deodorizing the liquid are effected simultaneously in the deodorizing absorbent sheet 1. In addition, as stated above, since the deodorizer 2 is fixed in the integrally formed sheet, there is no fear that the deodorizer 2 falls off in case it is incorporated in a large quantity in order to increase the deodorizing efficiency. This is particularly advantageous where black powder, etc. such as activated carbon is used as a deodorizer as hereinafter described.

Because the polymer 3 is also adhered and fixed to the fibers composing the fiber web 4, there is no fear of the polymer's falling off in case a large quantity of the polymer is incorporated to increase the absorption efficiency. This is particularly advantageous in obtaining a thin deodorizing superabsorbent sheet by incorporating an increased amount of the polymer 3 while reducing the thickness of the fiber web 4. In this case, while it is the most desirable for all the polymer 3 be fixed to the fibers, a sufficient effect for preventing fall-off could be exerted only if at least 50% by weight, especially 70% by weight or more, of the polymer 3 is fixed to the fibers.

While the weight ratio of the deodorizer 2 to the polymer 3 depends on the use, etc. of the deodorizing absorbent sheet 1, a generally preferred deodorizer to polymer weight ratio (the former/the latter) ranges from 1/10 to 10/1, particularly from 1/3 to 3/1 for the following reasons. The weight ratio being 1/10 or higher, a sufficient deodorizing effect is exhibited on the liquid absorbed by the polymer 3 and the liquid present thereabouts. The weight ratio being 10/1 or lower, the particles of the deodorizer 2 are sufficiently fixed with the polymer 3 and thereby prevented effectively from falling off the deodorizing absorbent sheet 1.

The amounts of the deodorizer 2 and the polymer 3 to be scattered are preferably determined so that their weight ratio may fall within the above-specified range. Specifically, the deodorizer 2 is preferably scattered in an amount of 3 to 500 g/m$^2$, particularly 20 to 100 g/m$^2$, and the polymer 3 is preferably scattered in an amount of 5 to 500 g/m$^2$, particularly 20 to 100 g/m$^2$. The deodorizer 2, scattered in an amount of 3 g/m$^2$ or more, manifests an effective deodorizing ability on liquid absorption. With the amount of the deodorizer not exceeding 500 gm$^2$, sufficient softness of the deodorizing absorbent sheet 1 can be secured, and the cost can be minimized. On the other hand, the polymer 3, scattered in an amount of 5 g/m$^2$ or more, the deodorizer 2 can be sufficiently fixed to the fiber web 4. With the amount of the polymer 3 not exceeding 500 g/m$^2$, drying of the sheet is conducted efficiently, and hindrance to absorption due to gel blocking can be prevented effectively.

The deodorizer 2 is not particularly limited in kind as long as it is insoluble in water and has a deodorizing function. Examples of useful deodorizers are particulate or fibrous activated carbon, natural minerals (e.g., bentonite, bentonite derivatives, kaolinite, and kanemite), and synthetic inorganic substances (e.g., zeolite and amorphous silica). Particulate activated carbon is preferred for its relative inexpensiveness and stable absorptivity for a variety of substances giving off a bad smell. In using a particulate deodorizer, a preferred particle size is 1 to 800 μm, particularly 50 to 600 μm, for prevention from falling off the fiber web 4 and for protection of the fiber web 4 against tearing.

The polymer 3 is preferably of material capable of absorbing and holding 20 times or more as heavy liquid as its own weight and capable of gelling. Such polymers include starch, crosslinked carboxymethylated cellulose, homo- or copolymers of acrylic acid or an alkali metal salt of acrylic acid, polyacrylic acid or a salt thereof, and a polyacrylic acid salt graft polymer. It is particularly preferred to use a particulate polymer having a particle size of 2 to 800 μm, especially 50 to 600 μm.

The fiber composing the fiber web 4 includes cellulosic fibers, such as natural cellulose, e.g., wood pulp and cotton, and regenerated cellulose, e.g., rayon and cuprammonium rayon. Filaments or staple fibers, etc. of thermoplastic fibers are also useful. From the standpoint of cost, wood pulp is preferred. Conifer kraft pulp (NBKP) is still preferred. It is particularly preferred that the fiber web 4 be formed predominantly of bulky fibers, especially bulky cellulosic fibers for facilitating permeation and diffusion of liquid. The term "bulky fibers" as used herein denotes fibers having a three-dimensional structure, such as a twisted structure, a crimped structure, a bent structure, a branched structure, and a combination thereof or very thick fibers whose degree of roughness is, for example, not less than 0.3 mg/m. By the term "fiber web" as used herein is meant sheeting formed by mechanical entanglement, adhesion or fusion among fibers, and the like. Such sheeting includes paper, nonwoven fabric, and composites thereof.

The bulky fibers include cellulosic fibers having a degree of roughness of 0.3 mg/m or more, particularly 0.3 to 2 mg/m. Cellulosic fibers having a degree of roughness of 0.3 mg/m or more and a degree of fiber roundness of 0.5 to 1 are also preferred. Crosslinked cellulosic fibers obtained by intermolecular and intramolecular crosslinking of cellulosic fibers are also preferred as bulky fibers. The "degree of roughness" as used for fibers is a measure of thickness of fibers having non-uniform thickness. It is measurable with, for example, a fiber roughness meter FS-200 manufactured by KAJANNI ELECTRONICS, Ltd.

Where the above-described cellulosic fibers are used to compose the fiber web 4, thermally fusible bonding fibers are preferably used in combination to obtain a fiber web with enhanced wet strength. The thermally fusible bonding fibers are preferably used in a proportion of 1 to 50% by weight, particularly 3 to 30% by weight, based on the fiber web 4. The thermally fusible adhesive fibers can be of a material capable of fusing upon heating to adhere to each other. Such fibers include those of polyolefin fibers, such as polyethylene, polypropylene and polyvinyl alcohol; polyester fibers; and conjugate fibers, such as those of polyethylene/polyester. Fibers of polyvinyl alcohol, polyester, etc. are particularly preferred. The thermally fusible bonding fibers usually have a length of 2 to 60 mm and a diameter of 0.5 to 3 denier.

The fiber web 4 preferably has a basis weight of 10 to 200 g/m$^2$, particularly 15 to 100 g/m$^2$. The total basis weight of the deodorizing absorbent sheet 1 is preferably 50 to 500 g/m$^2$, particularly 60 to 300 g/m$^2$, from the viewpoint of cost performance in wet strength, absorptivity, and deodorizing ability.

Figure 2:
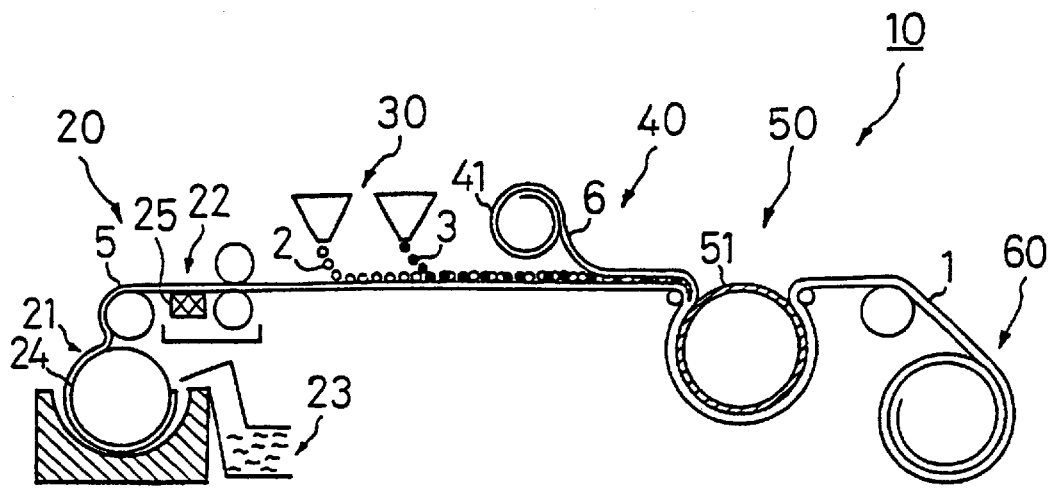
FIG. 2 is a schematic view illustrating the apparatus that is preferably used in producing the deodorizing absorbent sheet of the present invention.

A preferred process for producing the deodorizing absorbent sheet 1 will be illustrated by referring to FIG. 2.

The apparatus 10 shown in FIG. 2 comprises a part 20 for forming a lower fiber sheet, a part 30 for scattering powder, a part 40 for superposition, a drying part 50, and a take-up part 60.

The lower sheet forming part 20 has a paper-making part 21 and a dehydration part 22. A slurry from a paper stock feeding part 23 is fed to the paper-making part 21, where a lower fiber sheet 5 is formed on a cylinder 24. The lower fiber sheet, which contains a large amount of water, is dehydrated in a suction box set in the dehydration part 22 to provide a wet lower fiber sheet 5 having a prescribed water content. The water content of the wet lower fiber sheet 5 is preferably in a range of from 20 to 500% by weight, particularly 50 to 300% by weight, for the following reasons. The lower fiber sheet 5 having a water content of 20% by weight or more, an absorbent polymer scattered thereon becomes sufficiently tacky to fix itself and to fix a deodorizer. With the water content not exceeding 500% by weight, the lower fiber sheet 5 can be dried sufficiently in the drying part 50. The lower fiber sheet 5 preferably has a dry basis weight of 10 to 200 g/m$^2$, particularly 15 to 100 g/m$^2$.

In the powder scattering part 30, a deodorizer 2 and a polymer 3 are scattered on the wet lower fiber sheet 5 either simultaneously or in order, whereby the polymer 3 absorbs water to get tacky and is adhered and fixed to the fibers constituting the lower fiber sheet 5. Further, the deodorizer 2 is adhered to the tacky polymer 3 and thereby fixed to the fibers via the polymer 3.

Since the fibers constituting the lower fiber sheet 5 still have freedom while wet, being unbound to each other, the scattered deodorizer 2 and polymer 3 embed themselves in the interstices formed by the fibers and dispersed in three-dimensional manner. Therefore, larger amounts of a deodorizer and a polymer can be fixed stably as compared with a conventional sheet having a polymer and a deodorizer held in between two sheets of paper. The deodorizer 2 and the polymer 3 can be scattered uniformly over the entire surface of the wet lower fiber sheet 5 or, according to necessity, they can be scattered in spaced stripes along the longitudinal direction or in spots.

As to the order of scattering the deodorizer 2 and polymer 3 in the powder scattering part 30, the deodorizer 2 can precede the polymer 3 or vice versa, or they can be scattered simultaneously.

In the superposition part 40, a previously prepared dry upper fiber sheet 6 is unrolled from a feed roll 41 and superposed on the lower fiber sheet 5 having the deodorizer 2 and polymer 3 scattered thereon. The deodorizer 2 and polymer 3 are thus sandwiched between the upper fiber sheet 6 and the lower fiber sheet 5. In this stage, since the lower fiber sheet 5 is still in a wet state with the constituent fibers having freedom, the deodorizer 2 and polymer 3 are embedded deeper in the lower fiber sheet 5, and the fibers of the lower fiber sheet 5 and those of the upper fiber sheet 6 get entangled with each other easily. The upper fiber sheet 6 and the lower fiber sheet 5 may be the same or different in composition, which depends on the end use of the resulting deodorizing absorbent sheet, and the like. The upper fiber sheet 6 may be of various types of nonwoven fabric, such as air-through nonwoven fabric, spunbonded nonwoven fabric, and spunlaced nonwoven fabric.

The lower fiber sheet 5 having overlaid with the upper fiber sheet 6 was then sent to a Yankee drier 51, where it is dried so that the fibers of the upper and lower fiber sheets 5 and 6 are further entangled to unit the upper and lower fiber sheets 5 and 6 into a fiber web 4. Hydrogen bonding and heat fusion back up the uniting into a unitary body. At the same time, fixation of the deodorizer 2 and polymer 3 further proceeds while drying. There is thus obtained a deodorizing absorbent sheet of a single sheet structure having the deodorizer 2 and polymer 3 embedded in the fiber web 4. The drying temperature, while dependent on the kind of the fiber, etc., is usually 100 to 180° C., particularly 105 to 150° C. The resulting deodorizing absorbent sheet 1 is taken up in roll in the take-up part 60.

In a conventional process for producing a deodorizing sheet using wet-processed paper, activated carbon is previously mixed and dispersed together with pulp in the paper stock feeding part 23 and fed in the mixed state. To the contrary, it is a unique characteristic of the above-described process of the invention that the deodorizer is scattered on a fiber web while the latter is wet, which produces the following effects. (1) The sheet strength is not impaired. (2) The deodorizer does not show up on the sheet surface. (3) The deodorizer and the polymer are anchored and embedded in the fiber web.

The deodorizing absorbent sheet of the present invention thus obtained is suitably used as not only an absorbent member of absorbent articles, such as sanitary napkins and disposable diapers but an underlay for a pet's toilet, an absorbent sheet used in keeping and/or thawing frozen foods, a deodorant sheet for a toilet seat, a deodorant core of bedclothes, and deodorant wallpaper.

While the deodorizing absorbent sheet of the present invention has been described with particular reference to its preferred embodiments, it should be understood that the present invention is not construed as being limited thereto, and various changes and modifications can be made therein without departing from the scope thereof. For instance, the deodorizing absorbent sheet 1 can be made to perform additional functions by incorporating various substances, such as hydrophilic fine fibers or hydrophilic particles serving for improvement on absorptivity, into the part where a mixture of the deodorizer 2 and the polymer 3 is embedded. Further, a paper strengthening agent, such as sponge or carboxymethyl cellulose, can be added to the lower and/or upper fiber sheet(s) to increase the wet strength. Further, the wet upper sheet may be overlaid on the lower sheet instead of overlaying the dry upper sheet.

EXAMPLE 1

Ninety-five parts of bulky crosslinked pulp having a degree of roughness of 0.32 mg/m and a degree of fiber roundness of 0.30 and 5 parts of polyvinyl alcohol fibers having a thickness of 1 denier and a length of 3 mm (FIBRIBOND (a trade name), produced by SANSHO K.K.) were dispersed and mixed in water to prepare a paper stock having a prescribed concentration. The stock was fed to the paper-making part of a wet paper machine to form a lower fiber sheet having a dry basis weight of 20 g/m$^2$. The lower fiber sheet was dehydrated in a suction box to reduce the water content to 60% by weight. An absorbent polymer having a particle size of 300 μm was scattered almost uniformly on the dehydrated and still wet fiber sheet in an amount of 30 g/m², and activated carbon having a particle size of 300 μm was then scattered almost uniformly in an amount of 3 g/m². An upper fiber sheet of an absorbent paper (basis weight: 40 g/m²) having the same composition as the lower fiber sheet which had previously been made was superposed on the lower fiber sheet having the polymer and activated carbon scattered on. The lower fiber sheet having overlaid with the absorbent paper was passed through a Yankee drier, where it was dried at 130° C. and united into a unitary body. There was obtained a single deodorizing absorbent sheet having the polymer and activated carbon mixed and embedded therein. The basis weight of the resulting sheet was 93 g/m².

EXAMPLE 2

A deodorizing absorbent sheet was obtained in the same manner as in Example 1, except for changing the amount of the activated carbon to be scattered to 90 g/m².

EXAMPLE 3

A deodorizing absorbent sheet was obtained in the same manner as in Example 1, except that 3 g/m² of bentonite having a particle size of 100 μm or smaller was additionally scattered.

EXAMPLE 4

A deodorizing absorbent sheet was obtained in the same manner as in Example 1, except for replacing the bulky crosslinked pulp used in the upper and lower fiber sheets with bulky conifer kraft pulp (NBKP) having a degree of roughness of 0.24 mg/m and a degree of fiber roundness of 0.34 (HARMac-R, produced by MacMilan Bloedel Ltd.), and changing the amount of the activated carbon to be scattered to 30 g/m².

COMPARATIVE EXAMPLE 1

The same amounts of the same absorbent polymer and activated carbon as used in Example 1 were scattered on a dry lower fiber sheet having the same composition and basis weight as those of the lower fiber sheet used in Example 1. A dry upper fiber sheet having the same composition and basis weight as those of the upper fiber sheet used in Example 1 was superposed thereon. Two sheets were heated to 130° C. to obtain a comparative deodorizing absorbent sheet. The resulting sheet was not a single sheet having the upper and lower fiber sheets joined together but a 2-ply sheet.

Evaluation of Performance

In order to evaluate the performance of the deodorizing absorbent sheets obtained in Examples and Comparative Example, the deodorizing effect and fall-off of the deodorizer and the absorbent polymer were measured, and the absorptivity of the sheet in use as a napkin was evaluated in accordance with the following test methods.

1) Deodorizing Effect

In a 500 ml Erlenmeyer flask with a glass stopper was injected 5 μl of diethylamine with a microsyringe, and the flask was closed with the stopper (this sample is referred to as control 1). A piece 5 cm by 5 cm was cut out of the deodorizing absorbent sheet and put in a bag made of nonwoven fabric, which was used as a test piece. The test piece was put into another Erlenmeyer flask containing diethylamine, and the flask was closed with the stopper. After 30 minutes, the intensity of the smell was measured as follows.

A closed Erlenmeyer flask containing each test piece, a control Erlenmeyer flask, and an Erlenmeyer flask containing nothing (control 2) were presented, and 25 test users chosen at random were asked to evaluate the smell. The results of evaluation were averaged. The indices of evaluation and what is meant by an average of evaluation are as follows.

Manner of Evaluation (1) The control 2 (odorless flask), with the glass stopper removed, is first smelled at;

(2) Immediately after (1), the flask containing a test piece is smelled at similarly; then (3) The control 1 is then swelled at similarly.

After (1), (2) and (3), the test users choose what they think is the closest to what they feel from the following indices. Testing a sample is followed by testing another in the order of (1), (2) and (3).

Indices of Evaluation

1 Totally equal to the control 2 (odorless).

2 Almost odorless.

3 Smelling slightly.

4 Smelling like the control 1.

Meaning of Average Value

The smaller the value, the higher the deodorizing effect, meaning that the smell of the contents of the flask has been absorbed.

2) Absorptivity

Figure 3:
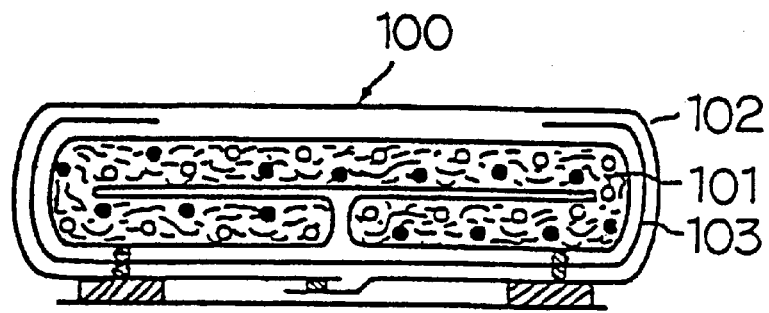
FIG. 3 is a cross-sectional view showing the structure of the sanitary napkin used in evaluating absorptivity.
Figure 4:
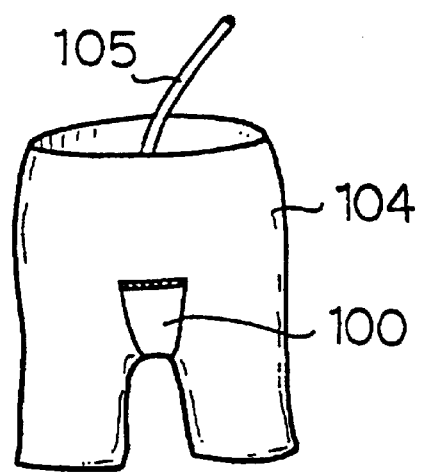
FIG. 4 is a schematic view of a movable model of female hips, which was used in evaluating absorptivity.

Sanitary napkins shown in FIG. 3 were prepared by using the deodorizing absorbent sheet obtained in Examples and Comparative Example. FIG. 3 is a cross-section of a sanitary napkin 100. The napkin 100 is composed of an absorbent member 101 that is formed by folding a deodorizing absorbent sheet in the manner shown, a topsheet 102 that is of perforated polyethylene film (perforation ratio: 20%) and envelopes the upper and lower sides of the absorbent member 101, and a backsheet 103 that is of polyethylene laminated waterproof paper. The napkin 100 was attached to a movable model of female hips 104, and sanitary panties were put on. The model was made to take a walking movement at a speed of 100 steps/min for 10 minutes (corresponding to a walking speed of 50 m/min). The model 104 being kept in a moving mode, 5 g of defibrinated horse blood was injected into the sanitary napkin through a tube 105, and the walking movement was continued for 20 minutes at the same speed (5 g-absorption point). Then, 5 g of defibrinated horse blood was again injected, followed by additional 20 minutes' movement at the same speed (10 g-absorption point). The number of the napkins out of ten subjected to testing which had a leak at each time point was taken as an index of absorptivity.

3) Fall-off of Deodorizer and Polymer

A sample piece of the sheet cut to a size of 70 mm by 200 mm was weighed and put in a plastic bag 280 mm long and 200 mm wide with a zipper. The bag was shaken 50 times in a hand to give vibrations to the sample. After the test, the sample was again weighed. The difference of the weight before the test and that after the test was taken as the amount of the fallen deodorizer and polymer. The sample after the test was also observed with the naked eye. The results of the measurement and observation were rated as followed.

A Almost no fall-off of the deodorizer and polymer was observed (equal to or less than 0.05 g).

B Slight fall-off of the deodorizer and polymer was observed (more than 0.05 g and less than 0.15 g).

C Considerable fall-off of the deodorizer and polymer was observed (equal to or more than 0.15 g).

TABLE 1

| | Deodorize | | | | Fall-off of Deodorizer and Polymer | | | Absorptivity (Number of Leaks) | |
|---|---|---|---|---|---|---|---|---|---|
| | Kind | Particle Size (μm) | Scattered Amount (g/m²) | Deodorizer/ Polymer | Deodorizing Effect (Odor Intensity) | Fallen Amount (g) | Observation with Eye | 5 g | 10 g |
| Example 1 | activated carbon | 300 | 3 | 1/10 | 2.2 | ≦0.01 | A | 0 | 0 |
| Example 2 | activated carbon | 300 | 90 | 3/1 | 1.1 | 0.03 | A | 0 | 0 |
| Example 3 | activated carbon bentonite | 300 ≦100 | 3 3 | 2/10 | 2.0 | ≦0.01 | A | 0 | 0 |
| Example 4 | activated carbon | 300 | 30 | 1/1 | 1.6 | 0.03 | A | 0 | 0 |
| Comparative Example 1 | activated carbon | 300 | 3 | 1/10 | 2.2 | 0.21 | C | 0 | 2 |

As is apparent from the results shown in Table 1, it is seen that the deodorizing absorbent sheets of Examples (invention) are superior to the comparative sheet in deodorization and absorption. Although the sheets of the present invention contains large amounts of the deodorizer and the polymer, these particles hardly fall off the sheets.

INDUSTRIAL APPLICABILITY

As hereinabove described in detail, the present invention provides a deodorizing absorbent sheet having a high deodorizing function and a high absorbing function.

The present invention also provides a deodorizing absorbent sheet which can contain large amounts of a deodorizer and a polymer and yet involves no fear of these particles' falling off.

What is claimed is:

1. A deodorizing sheet having a water-insoluble deodorizer and an absorbent polymer which are embedded in a fiber web, in which said absorbent polymer is fixed to the fibers making up said fiber web, and said deodorizer is fixed inside said fiber web via said absorbent polymer, said deodorizer and said absorbent polymer being substantially absent on the surface of said sheet, said dedorizer being particulate and having a particle size of 50 to 600 μm and said absorbent polymer being a particulate polymer having a particle size of 50 to 600 μm.

2. The deodorizing absorbent sheet according to claim 1, wherein the weight ratio of the deodorizer to the absorbent polymer is 1/10 to 10/1.

3. The deodorizing absorbent sheet according to claim 1, wherein the fiber web is formed predominantly of bulky cellulosic fibers.

4. A process for producing the deodorizing absorbent sheet as set forth in claim 1, the process comprising the steps of scattering the absorbent polymer and the deodorizer on a wet lower fiber sheet either simultaneously or successively in any order, overlaying an upper fiber sheet thereon, and uniting the upper and lower fiber sheets into a unitary body by drying.

5. The deodorizing absorbent sheet of claim 1, wherein the weight ratio of the deodorizer to the absorbent polymer is 1/3 to 3/1.

6. The deodorizing absorbent sheet of claim 1, wherein said absorbent polymer is present in the amount of 20 to 100 g/m².

7. The deodorizing absorbent sheet of claim 1, wherein said deodorizer is present in the amount of 20 to 100 g/m².

8. The deodorizing absorbent sheet of claim 1, wherein said absorbent polymer is present in the amount of 3 to 500 g/m² and said deodorizer is present in the amount of 3 to 500 g/m².

9. The deodorizing absorbent sheet of claim 1, wherein said deodorizer is selected from the group consisting of activated carbon, a natural mineral and a synthetic inorganic substance.

10. The deodorizing absorbent sheet of claim 9, wherein said deodorizer is activated carbon.

11. The deodorizing absorbent sheet of claim 3, wherein said bulky cellulosic fibers in the fiber web has a degree of roughness of 0.3 mg/m to 2 mg/m.

12. The deodorizing absorbent sheet of claim 3, wherein said bulky cellulosic fibers in the fiber web has a degree of fiber roundness of 0.5 to 1.

13. The deodorizing absorbent sheet of claim 1, wherein said fiber web has a basis weight of 15 to 100 g/m².

14. The deodorizing absorbent sheet of claim 1, wherein the deodorizing absorbent sheet has a basis weight of 50 to 500 g/m².

* * * * *